United States Patent [19]

Dobson

[11] 4,269,683

[45] May 26, 1981

[54] ELECTROCHEMICAL MEASURING SYSTEM

[75] Inventor: John V. Dobson, Hartlepool, England

[73] Assignee: National Research Development Corporation, London, England

[21] Appl. No.: 45,650

[22] Filed: Jun. 5, 1979

[30] Foreign Application Priority Data

Jun. 19, 1978 [GB] United Kingdom ............ 27235/78

[51] Int. Cl.³ ............................................. G01N 27/46
[52] U.S. Cl. ................................ 204/195 W; 204/1 T; 204/195 R; 324/71 R
[58] Field of Search ............ 204/195 W, 1 W, 195 R; 324/439, 65 R, 71 R

[56] References Cited

U.S. PATENT DOCUMENTS

| | | | |
|---|---|---|---|
| 1,865,847 | 7/1932 | Ennis | 204/195 R X |
| 2,651,612 | 9/1953 | Haller | 204/195 R |
| 3,103,481 | 9/1963 | Robinson | 204/195 R |
| 3,562,353 | 8/1969 | Every et al. | 204/147 |
| 3,743,589 | 7/1973 | Nicholas | 204/195 R |

OTHER PUBLICATIONS

P. Hersch, "Galvanic Analysis", p. 237, Reprint 6213, Beckman Instruments, (1964).

J. V. Dobson et al., Electrochemica. Acta. 21, 527–553, (1976).

*Primary Examiner*—G. L. Kaplan
*Attorney, Agent, or Firm*—Oblon, Fisher, Spivak, McClelland & Maier

[57] ABSTRACT

An electrochemical measuring system is used to determine the proportion of water in ethanol, or of moisture in carbon powder, and consists of a $Pb/PbO_2/PbSO_4$ electrode and a $Pt/PtO_2$ electrode in the ethanol or powder, with a high impedance voltmeter connecting the electrodes.

7 Claims, No Drawings

ELECTROCHEMICAL MEASURING SYSTEM

This invention relates to an electrochemical measuring system and to a method of determining the presence of a polar liquid such as water, using the system.

According to this invention, such a system comprises a first electrode and a second electrode connected to input of a voltmeter; the first electrode consists of a first metal in contact with its oxide; the second electrode consists of a second metal (different from the first metal) in contact with its oxide; the first and second metals are any two of platinum, lead, nickel, rhodium, iridium and zirconium. The first metal may be lead, and the lead dioxide $PbO_2$ may also contain lead sulphate $PbSO_4$, in a dioxide:sulphate weight ratio of preferably 5:1 to 15:1.

The second metal is preferably platinum.

The voltmeter preferably has an impedance of at least $10^6$ ohm, better still at least $10^{12}$ ohm.

Another aspect of this invention is a method of determining the proportion of a polar liquid in a non-polar (i.e. less polar) liquid, comprising placing therein the electrodes of a system as set forth above and comparing the voltmeter reading with readings obtained with standard solutions of the polar liquid in the non-polar liquid. The polar liquid may be water, and the non-polar liquid may be an organic liquid. The comparison may consist in previously calibrating and/or biassing the voltmeter to zero so that it reads out directly in units of concentration of polar liquid or water. There is also provided a method of determining the moisture content of a powder, comprising placing therein the electrodes of the system as set forth above, and comparing the voltmeter reading with readings obtained with like powders of known moisture content.

The metal/metal oxide electrodes above have been notorious for irreproducibility, but in non-aqueous solvents, and in the absence of oxygen, and when they have been calibrated, they display a useful sensitivity. Since the above electrodes each have a different response to (for example) water, the resultant e.m.f. which they produce is proportional to the activity of the water.

For some time, industries concerned with organic solvents have had to rely, for measuring moisture contents, on unreliable electrical conductivity methods or other imprecise or indirect methods, which are generally insensitive to amounts of less then a few percent of water or in mixtures of solvents. However, in chemical processes involving solvents, and for example in the industrial production or use of alkali metals, the presence of even fractions of a percent of water could be disastrous in some plants.

The principles of operation of the invention will be discussed in specific terms, for purposes of illustration only, the scope of the invention being as set forth above.

The lead/lead dioxide electrode is sensitive to the activity of water, by way of the reaction.

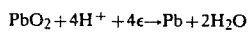

$$PbO_2 + 4H^+ + 4e \rightarrow Pb + 2H_2O$$

Usually this water activity is considered a nuisance when the lead/lead dioxide/lead sulphate electrode is being used for its main purpose, that is a $SO_4^=$ reversible ion electrode. This 'nuisance' is put to use in the present invention for measuring the activity coefficient of water in organic solvents, and we have found that the activity coefficient of water varies rapidly with small increments of water. Because two electrodes are required to measure an e.m.f., a second or reference electrode is necessary, for example an electrode whose potential does not vary significantly with water activity, such as the Ag, AgCl electrode. The presence of ions in the 'moisture', to which either electrode is sensitive, could be a problem. To overcome this, it would be necessary to calibrate the probe in the presence of the relevant ion, e.g. chloride ion in the case of the AgCl, Ag electrode. This complication is avoided in this invention by choosing (for example) the electrode pair Pb, $PbO_2$, $PbSO_4$/Pt, $PtO_2$, or Pb, $PbO_2$/Pt, $PtO_2$, which though both displaying sensitivities to water, do so to different extents. Their differing pH sensitivities have a negligible effect or can be easily accommodated. Alternatively, it is possible that, as a moisture meter, the system functions via the effect of a change in pH and not water activity, because water may affect the organic solvent's dielectric constant, which in turn affects the ionization constant of water, and hence the pH.

As regards sensitivities to other ions such as sulphate and chloride, we are considering measurements in organic solvents which contain very small amounts of water. Even if present, such ions would therefore possibly be salted out and hence should only cause a small problem.

The invention will now be described by way of example.

A lead/lead oxide/lead sulphate electrode is prepared as follows. Powdered lead dioxide and lead sulphate are sieved separately through 200 BSS sieves. The powder which passes through the sieves is mixed together in the proportion 9:1 (dioxide:sulphate) by weight and the mix placed in a jar with a quantity of small lead shot. This is tumbled for 48 hours, after which it is sieved once more (−200 BSS), to retrieve the lead shot. Pellets may be formed from the mixed powders either by pressure alone or by the addition of a small amount of bonding resin. The details that follow describe the use of pressure alone to form the pellet which, however, is subsequently set in resin for the construction of the electrode as a whole.

The powder is pressed into a pellet of approximately 5 mm diameter × 5 mm thick in a die under a pressure of 2 tons. A piece of lead wire of 3 mm diameter is then formed into a ring of just over 6 mm internal diameter, and the pellet is placed in the centre of this ring in a larger die and pressed under a pressure of 10 tons. The resultant disc is very sturdy and can be filed, abraded or polished fairly safely. The disc is then mounted in the electrode body as follows.

Tinned copper wire is soldered to one face of the lead, and that face, and the first few millimeters of the wire, are embedded in an epoxy resin (chosen to resist the solvent in which the electrode is to be used), leaving only the opposite face of the pellet exposed.

The assembly is machined to be screwable into an electrode holder up the axis of which the copper wire passes to a voltmeter. A sealing ring compressed between the assembly and the electrode holder prevents ingress of liquid.

The electrical resistance of a typical disc is between 50 ohm cm$^{-1}$ and 100 ohm cm$^{-1}$.

The overall cohesion of a typical disc is fully adequate, and even if the assembly is left in 50:50 acetone/water for several weeks, no change is discernible.

A reference Pt/$PtO_2$ electrode was made from a platinum wire with the tip oxidised (e.g. by heating in oxygen to above 500° C. or in KNO$_3$ at 400° C.). The non-oxidised end of the platinum wire is connected to the other side of the voltmeter, which, together with a buffer amplifier in series with it, has an impedance of 10$^{15}$ ohm.

EXPERIMENT 1

A 50 ml sample of ethanol which had been dried using calcium oxide was placed in a beaker, protected by a cover from atmospheric oxygen, with two electrodes in it. Thanks to the high impedance of the voltmeter, the spacing between the electrodes assumes negligible importance. The voltmeter was found to give a deflection corresponding to −0.201 V (Pb negative).

Distilled water was added to the beaker, through a small hole in the cover, in 0.2 ml aliquots. The solution was stirred constantly.

After successive additions, the e.m.f. was −0.221 V, −0.237 V, −0.245 V, −0.254 V and −0.259 V. Thereafter the e.m.f. increases more linearly. The sensitivity of the system can thus be seen to be greatest at the lowest water concentrations. By biassing the voltmeter to zero at zero water, a direct reading of water content could be obtained, and, as the response is linear over small ranges of water contents, the voltmeter could be calibrated in experiments using standard solutions in the relevant range.

EXPERIMENT 2

Experiment 1 was repeated, but using, instead of pure ethanol, a dried mixture of ethanol (25 ml) and acetone (25 ml). This gave a voltmeter reading of −0.036 V (Pb negative). Successive additions of 0.2 ml aliquots of distilled water gave readings of −0.064 V, −0.096 V, −0.112 V, −0.128 V and −0.144 V, and thence nearly linearly at a gently decreasing slope up to around 5% water.

In both Experiments, a maximum reading was obtained from the voltmeter within about 15 seconds from the addition of the aliquot.

EXPERIMENT 3

The two electrodes were placed spaced apart in dry carbon powder. Thanks to the high impedance of the voltmeter, the high conductivity of the powder was rendered harmless. The voltmeter reading was noted.

The two electrodes were dusted clean and placed at the same spacing in a sample of damp carbon powder. A very different voltmeter reading was obtained.

Thus, this system can be used, following calibration/standardisation, to indicate the moisture content of powders. It would be possible to do this in a continuous stream such as might be encountered in a manufacturing process.

I claim:

1. An electrochemical measuring apparatus, comprising: a lead electrode in contact with its oxide containing sulfate and a second electrode being of a metal selected from the group consisting of platinum, nickel, rhodium, iridium and zirconium in contact with its oxide, both electrodes being connected to opposite sides of a voltmeter.

2. The apparatus according to claim 1, wherein the oxide:sulfate weight ratio is 5:1 to 15:1.

3. The apparatus according to claim 1, wherein the metal of said second electrode is platinum.

4. The apparatus according to claim 1, wherein the voltmeter has an impedance of at least 10$^6$ ohm.

5. The apparatus according to claim 4, wherein the voltmeter has an impedance of at least 10$^{12}$ ohm.

6. An electrochemical measuring apparatus, comprising:
a lead electrode in contact with its oxide containing lead sulfate and a platinum electrode in contact with its oxide, both electrodes being connected to opposite sides of a voltmeter.

7. The apparatus of claim 6, wherein the oxide:sulfate weight ratio of said lead electrode is 5:1 to 15:1.

* * * * *